(12) United States Patent
Cheng et al.

(10) Patent No.: US 8,992,577 B2
(45) Date of Patent: *Mar. 31, 2015

(54) ROD SYSTEM FOR GRADUAL DYNAMIC SPINAL FIXATION

(71) Applicant: Tongji University, Shanghai (CN)

(72) Inventors: Liming Cheng, Shanghai (CN); Yan Yu, Shanghai (CN); Zhili Zeng, Shanghai (CN); Wei Xu, Shanghai (CN); Yongwei Jia, Shanghai (CN); Lie Qian, Shanghai (CN); Rui Zhu, Shanghai (CN); Jianjie Wang, Shanghai (CN); Zhourui Wu, Shanghai (CN)

(73) Assignee: Tongji University, Shanghai (CN)

( * ) Notice: Subject to any disclaimer, the term of this patent is extended or adjusted under 35 U.S.C. 154(b) by 6 days.

This patent is subject to a terminal disclaimer.

(21) Appl. No.: 14/208,877

(22) Filed: Mar. 13, 2014

(65) Prior Publication Data
US 2014/0194931 A1 Jul. 10, 2014

Related U.S. Application Data

(63) Continuation of application No. 13/376,502, filed as application No. PCT/CN2010/076195 on Aug. 20, 2010, now Pat. No. 8,709,048.

(51) Int. Cl.
A61B 17/70 (2006.01)
A61B 17/00 (2006.01)

(52) U.S. Cl.
CPC ......... *A61B 17/7026* (2013.01); *A61B 17/7023* (2013.01); *A61B 17/7025* (2013.01); *A61B 17/7004* (2013.01); *A61B 17/7031* (2013.01); *A61B 2017/00004* (2013.01)
USPC ........................... 606/257; 606/256; 606/259

(58) Field of Classification Search
CPC ........... A61B 17/7035; A61B 17/7038; A61B 17/7019; A61B 17/702; A61B 17/7023
USPC ............. 606/246–261, 278; 623/17.11–17.16
See application file for complete search history.

(56) References Cited

U.S. PATENT DOCUMENTS 7,326,210 B2    2/2008   Jahng et al.
7,686,833 B1    3/2010   Muhanna et al.
(Continued)

FOREIGN PATENT DOCUMENTS

CN    1463678 A    12/2003
CN    1286435 C    11/2006
(Continued)

OTHER PUBLICATIONS

Notice of Allowance dated Dec. 18, 2013 in U.S. Appl. No. 13/376,502, filed Dec. 6, 2011.
(Continued)

*Primary Examiner* — Mary Hoffman
*Assistant Examiner* — Christina Negrellirodriguez
(74) *Attorney, Agent, or Firm* — Knobbe Martens Olson & Bear LLP

(57) ABSTRACT

A rod system includes two rods each with a head and a shaft, two elastic members each fitted around one shaft against one head, and a case defining a first inner portion, a second inner portion, and a third inner portion in communication with the first and the second inner portions. A first rod with a first elastic member is seated in the first inner portion so the first elastic member abuts the bottom of first inner portion and the first head protrudes into the third inner portion. A second rod and a second elastic member is seated in the second portion so the second elastic member abuts the bottom of the second inner portion and the second head protrudes into the third inner portion and abuts the first head.

16 Claims, 6 Drawing Sheets

(56) References Cited

U.S. PATENT DOCUMENTS

| | | | |
|---|---|---|---|
| 7,763,048 | B2 | 7/2010 | Fortin et al. |
| 7,776,071 | B2 | 8/2010 | Fortin et al. |
| 8,287,571 | B2 * | 10/2012 | Semler et al. ............ 606/254 |
| 8,709,048 | B2 | 4/2014 | Cheng et al. |
| 2005/0165396 | A1 | 7/2005 | Fortin et al. |
| 2005/0261685 | A1 | 11/2005 | Fortin et al. |
| 2007/0233073 | A1 | 10/2007 | Wisnewski et al. |
| 2008/0015578 | A1 | 1/2008 | Erickson et al. |
| 2008/0262554 | A1 | 10/2008 | Hayes et al. |
| 2010/0036423 | A1 | 2/2010 | Hayes et al. |
| 2010/0094424 | A1 | 4/2010 | Woodburn et al. |
| 2010/0114167 | A1 | 5/2010 | Wilcox et al. |
| 2013/0261667 | A1 | 10/2013 | Cheng et al. |

FOREIGN PATENT DOCUMENTS

| | | | |
|---|---|---|---|
| EP | 1408860 | A1 | 4/2004 |
| FR | 2827498 | A1 | 1/2003 |
| FR | 2931354 | A1 | 11/2009 |
| FR | 2931354 | B1 | 5/2010 |
| JP | 2002224131 | A | 5/2001 |
| JP | 2005504566 | T | 2/2005 |
| WO | WO 03007828 | A1 | 1/2003 |
| WO | WO 2009153431 | A1 | 12/2009 |
| WO | WO 2010019791 | A2 | 2/2010 |

OTHER PUBLICATIONS

Office Action dated Aug. 22, 2013 in U.S. Appl. No. 13/376,502, filed Dec. 6, 2011.

PCT Search Report and Written Opinion dated Jun. 2, 2011 in Application No. PCT/CN2010/076195.

Self-design and Preliminary Application of Zygapophyseal Joint System in Patients with Lumbar Distability. 2007;11(4):254-259. (Original Chinese Article with English Abstract).

G. Perrin, A. Cristini. Prevention of adjacent level degeneration above a fused vertebral segment: Long term effect, after a mean follow-up of 8.27 years, of the dynamic intervertebral fixation as a protective technique for pathological adjacent disc. IMAST 2003.

Schmoelz W, Huber JF, Nydegger T, et al. Dynamic stabilization of the lumbar spine and its effects on adjacent segments: an in vitro experiment. J Spinal Disord Tech, 2003;16:418-23.

Sengupta DK, Mulholland RC. Fulcrum assisted soft stabilization system: a new concept in the surgical treatment of degenerative low back pain. Spine,2005;30(9):1019-1029.

Wilke HJ, Schmidt H, Werner K, et al. Biomechanical evaluation of a new total posterior-element replacement system. Spine,2006;31(24):2790-6.

Zhu Q, Larson CR, Sjovold SG, et al. Biomechanical evaluation of the Total Facet Arthroplasty System: 3-dimensional kinematics. Spine, 2007,32(1):55-62.

Website—Scient'x Alphatec Spine—Thoraco-Lumbar Fixation, http://www.scientx.com/product_thoracolumbarfixation_ttldynamicrod.php#, printed on Oct. 21, 2011.

* cited by examiner

ROD SYSTEM FOR GRADUAL DYNAMIC SPINAL FIXATION

REFERENCE TO RELATED APPLICATIONS

This application is a continuation of U.S. application Ser. No. 13/376,502, filed Dec. 6, 2011, which is the U.S. National Phase entry under 35 U.S.C. §371 of International Application PCT/CN2010/076195, filed Aug. 20, 2010, entitled "ROD SYSTEM FOR GRADUAL DYNAMIC SPINAL FIXATION," the entirety of which is incorporated herein.

BACKGROUND

Unless otherwise indicated herein, the approaches described in this section are not prior art to the claims in this application and are not admitted to be prior art by inclusion in this section.

During the 1960's, posterior pedicle fixation for vertebral body stabilization was commonly performed utilizing pedicle screws, hooks, and rods. This kind of rigid load bearing stabilization offered physicians the ability to address various patient morphologies. However, clinical experience suggested that rigid fixation does not comply with the dynamic nature of the spine and were leading to complications, including implant failure and accelerated degeneration of the adjacent levels. Subsequently dynamic semi-rigid fixation systems were introduced, such as those available from SCIENT'X of Bretonneux, France. Nonetheless, these systems do not offer the rigid support needed immediately post-operation for vertebral body fracture.

SUMMARY

In one or more embodiments of the present disclosure, a rod system includes two rods each with a head and a shaft, two elastic members each fitted around one shaft against one head, and a case defining a first inner portion, a second inner portion, and a third inner portion in communication with the first and the second inner portions. A first rod with a first elastic member is seated in the first inner portion so the first elastic member abuts the bottom of first inner portion and the first head protrudes into the third inner portion. A second rod and a second elastic member is seated in the second portion so the second elastic member abuts the bottom of the second inner portion and the second head protrudes into the third inner portion and abuts the first head.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
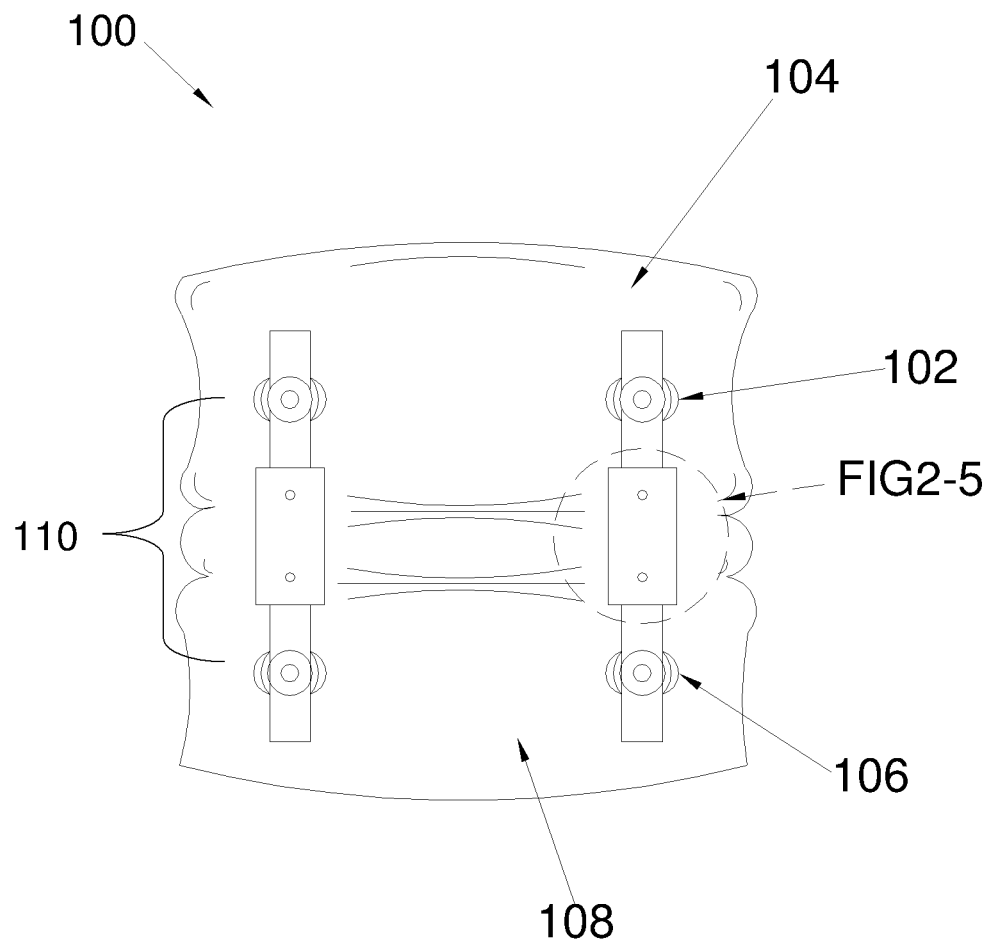
FIG. 1 is a perspective view of an illustrative bone fixation system attached to vertebrae.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

This disclosure is drawn, inter alia, to manufacturing methods, apparatus, systems, and techniques related to a dynamic rod system for a bone fixation system.

Bone screws are used in spinal instrumentation to manage bone fractures and correct deformity. For example, pedicle screws may provide a means of gripping a spinal segment, where a screw acts as a firm anchor point in one vertebra that can be connected to other such anchor points in other vertebrae with a rod. With two or more consecutive vertebrae fixated by such a construct, motion between the vertebrae is prevented or limited.

In one or more embodiments of the present disclosure, a rod system includes two rods held against each other by elastic members within a cylindrical case. Each rod is initially immobilized by a corresponding stopper made of an absorbable material so the rod system is rigid. The two rods are connected to two bone screws attached to two vertebrae. As the absorbable material is decomposed by bodily fluid introduced through holes in the cylindrical case, the corresponding rod gains mobility and the rod system becomes dynamic.

FIG. 1 is a perspective view of an illustrative bone fixation system 100 attached to vertebrae in one or more embodiments of the present disclosure. The bone fixation system 100 includes a first bone screw 102 attached on a first bone 104, a second bone screw 106 attached on a second bone 108, and a rod system 110 connected at two ends to the bone screws 102 and 106. The rod system 110 may initially form a rigid link between the bone screws 102 and 106 and then transition over time to a dynamic link between the bone screws 102 and 106. The bone screws 102 and 106 may be pedicle screws, and bones 104 and 108 may be vertebrae. The configuration is mirrored on both sides of the vertebrae.

Figure 2:
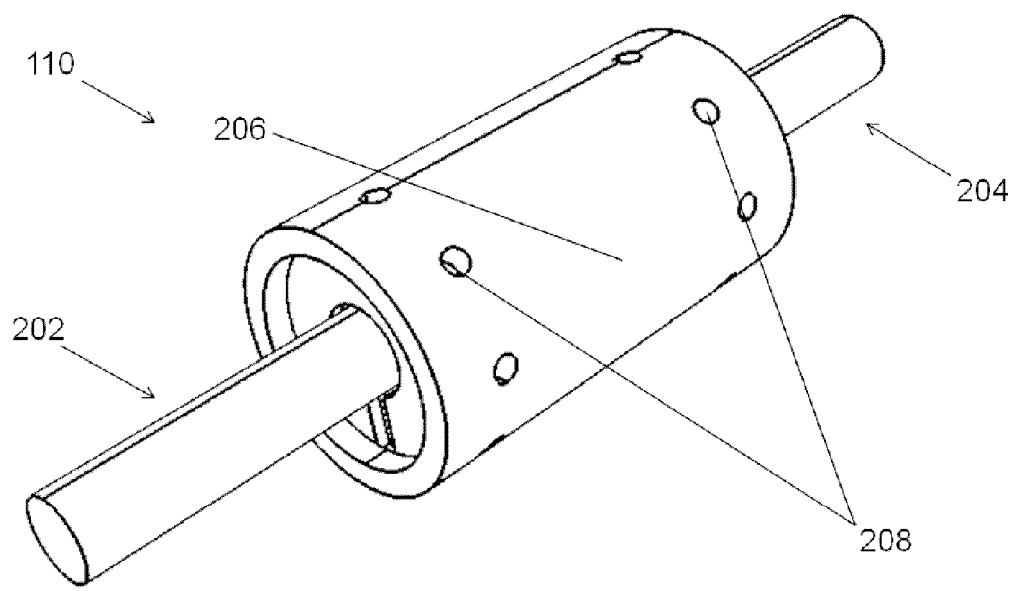
FIG. 2 is a perspective view of an illustrative dynamic rod system of the bone fixation system in FIG. 1.

FIG. 2 is a perspective view of an illustrative rod system 110 of the bone fixation system 100 in FIG. 1. The rod system 110 includes a first rod 202 and a second rod 204 extending from two ends of a cylindrical case 206. The first rod 202 is connected to the first bone screw 102 of FIG. 1 and the second rod 204 is connected to the second bone screw 106 of FIG. 1. The cylindrical case 206 defines two sets of through holes 208 around the circumference for introducing bodily fluid into the cylindrical case 206.

Figure 3:
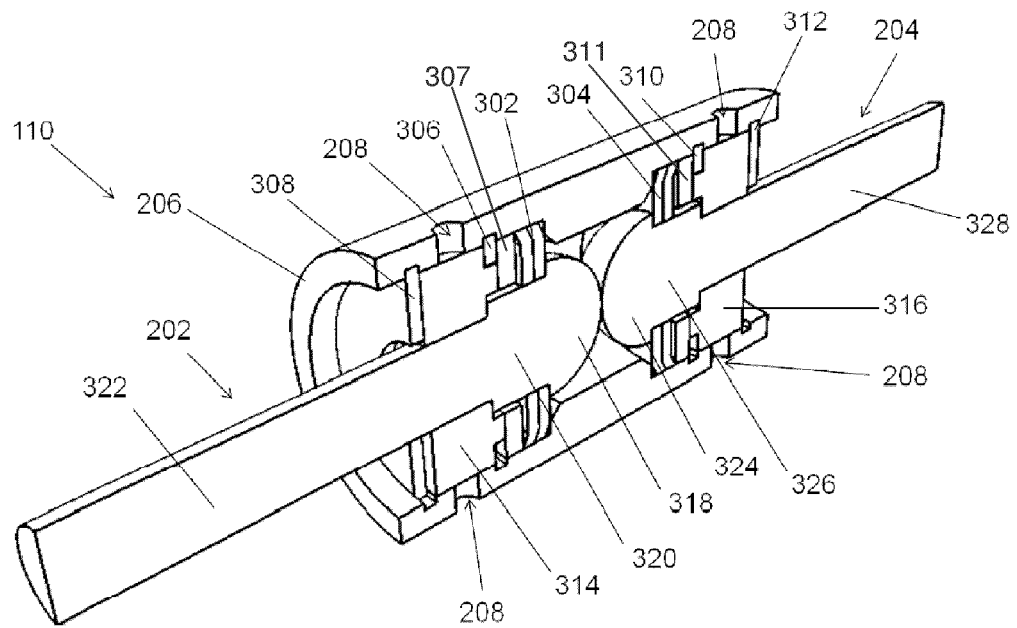
FIG. 3 is a perspective cross-sectional view of an illustrative rod system of FIG. 2.
Figure 4:
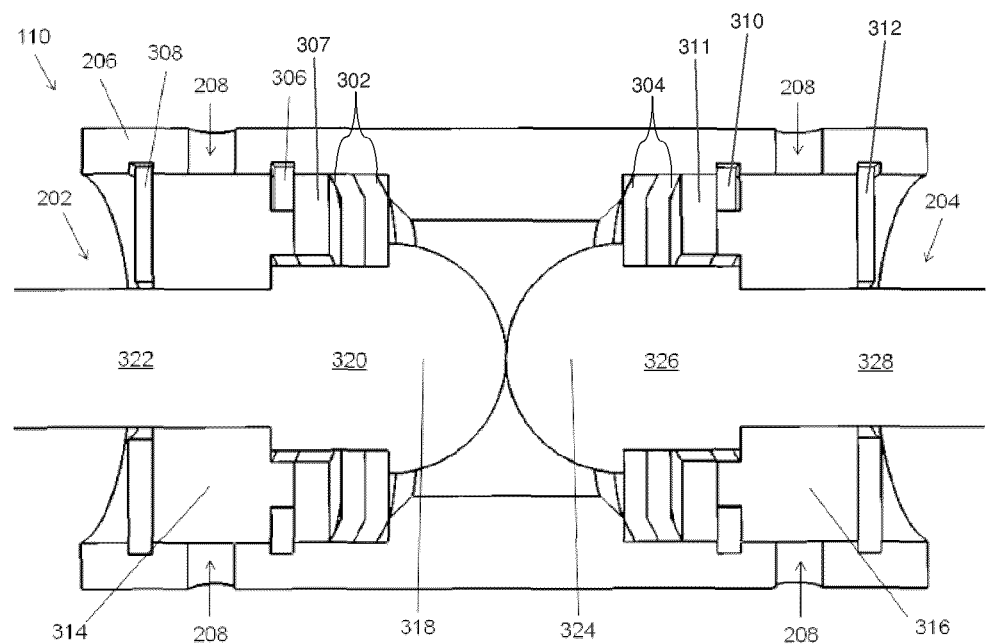
FIG. 4 is a partial side cross-sectional view of an illustrative rod system of FIG. 2.
Figure 5:
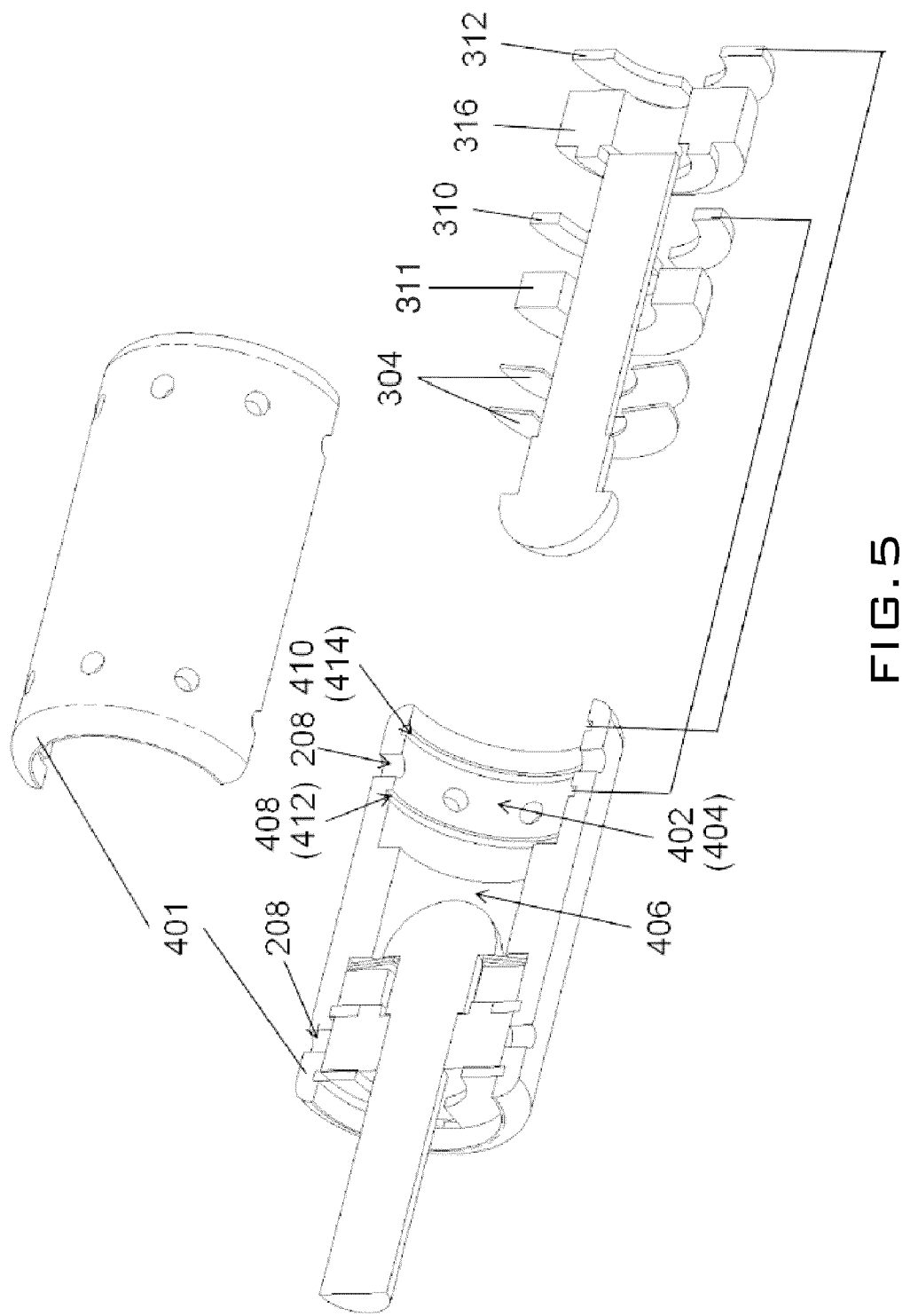
FIG. 5 is an exploded view of an illustrative rod system of FIG. 2.

The details of an illustrative rod system 110 are now explained in reference to FIGS. 3, 4, and 5, which show perspective cross-sectional view, a partial side cross-sectional view, and an exploded view of the rod system 110 in one or more embodiments of the present disclosure. The bone fixation system 100 includes the first rod 202, the second rod 204, first elastic members 302, second elastic members 304, a first retainer ring 306, a second retainer ring 308, a third retainer ring 310, a fourth retainer ring 312, a first stopper ring 314, a second stopper ring 316, a third stopper ring 307, a fourth stopper ring 311, and the cylindrical case 206. The first rod 202, the second rod 204, the first retainer ring 306, the second retainer ring 308, the third retainer ring 310, the fourth retainer ring 312, the third stopper ring 307, the fourth stopper ring 311, and the cylindrical case 206 may be made from metal that resist biological corrosions, such as titanium alloy and stainless steel.

Referring to FIGS. 4 and 5, the cylindrical case 206 includes two symmetrical halves 401 each defining a first counterbore 402 at one end for receiving the first rod 202, a second counterbore 404 at the other end for receiving the second rod 204, and a mid-bore 406 in communication with the counterbores 402 and 404. The first counterbore 402 includes an inner circumferential cutout 408 for receiving the first retainer ring 306, and an outer circumferential cutout 410 for receiving the second retainer ring 308. Similarly, the second counterbore 404 includes an inner circumferential cutout 412 for receiving the third retainer ring 310, and an outer circumferential cutout 414 for receiving the fourth retainer ring 312.

Referring generally to FIGS. 3 to 5, the first rod 202 includes a hemispheroid head 318, a neck 320 extending from the head 318, and a shaft 322 extending from the neck 320. The neck 320 has a smaller radius than the head 318, and the shaft 322 has a smaller radius than the neck 320.

In an embodiment, the first elastic members 302 and the second elastic members 304 may each include one or more elastic washers. The first elastic members 302 have an outer radius substantially the same as the radius of the first counterbore 402, and defines a hole having a radius substantially equal to the radius of the neck 320.

The third stopper ring 307 has an outer radius substantially the same as the radius of the first counterbore 402, and an inner radius substantially equal to the radius of the neck 320. The third stopper ring 307 is configured to be a stopping base of the first elastic members 302 and to limit the motion of the second rod 204.

The first retainer ring 306 has an outer radius substantially the same as the radius of the inner circumferential cutout 408, and an inner radius larger than the radius of the neck 320.

The first stopper ring 314 has an inner ring portion and an outer ring portion. In an embodiment, the inner ring portion has an outer radius substantially equal to the inner radius of the first retainer ring 306, and an inner radius substantially equal to the radius of the neck 320. The outer ring portion has an outer radius substantially equal to the radius of the first counterbore 402, and an inner radius substantially equal to the radius of the shaft 322. The first stopper ring 314 can be made of an absorbable material that is decomposed by bodily fluid, such as calcium phosphate and calcium sulphate.

The second retainer ring 308 has an outer radius substantially the same as the radius of the outer circumferential cutout 410, and an inner radius larger than the radius of the shaft 322.

The first rod 202 is inserted through the first elastic members 302, the third stopper ring 307, the first retainer ring 306, the first stopper ring 314, and the second retainer ring 308. The first elastic members 302 abut against the bottom of the head 318. The first retainer ring 306 fits around the inner ring portion of the first stopper ring 314, and both abut against the bottom of the first elastic members 302. The second retainer ring 308 abuts the bottom of the first stopper ring 314. The assembly is placed in one half 401 of the cylindrical case 206 so the head 318 protrudes into the mid-bore 406. The first elastic members 302 abut the bottom of the first counterbore 402. The first retainer ring 306 fits in the inner circumferential cutout 408, and the second retainer ring 308 fits in the outer circumferential cutout 410. Note that one set of through holes 208 are defined in the cylindrical case 206 around the first stopper ring 314.

Referring to FIGS. 3 to 5, the second rod 204 includes a hemispheroid head 324, a neck 326 extending from the head 324, and a shaft 328 extending from the neck 326. The neck 326 has a smaller radius than the head 324, and the shaft 328 has a smaller radius than the neck 326.

The second elastic members 304 have an outer radius substantially the same as the radius of the second counterbore 404, and defines a hole having a radius substantially equal to the radius of the neck 326.

The fourth stopper ring 311 has an outer radius substantially the same as the radius of the second counterbore 404, and an inner radius substantially equal to the radius of the neck 326. The fourth stopper ring 311 is configured to be a stopping base of the second elastic members 304 and to limit the motion of the first rod 202.

The third retainer ring 310 has an outer radius substantially the same as the radius of the inner circumferential cutout 412, and an inner radius larger than the radius of the neck 326.

The second stopper ring 316 has an inner ring portion and an outer ring portion. In an embodiment, the inner ring portion has an outer radius substantially equal to the inner radius of the third retainer ring 310, and an inner radius substantially equal to the radius of the neck 326. The outer ring portion has an outer radius substantially equal to the radius of the second counterbore 404, and an inner radius substantially equal to the radius of the shaft 328. The second stopper ring 316 is made of an absorbable material that is decomposed by bodily fluid, such as calcium phosphate and calcium sulphate.

The fourth retainer ring 312 has an outer radius substantially the same as the radius of the outer circumferential cutout 414, and an inner radius larger than the radius of the shaft 328.

The second rod 204 is inserted through the second elastic members 304, the fourth stopper ring 311, the third retainer ring 310, the second stopper ring 316, and the fourth retainer ring 312. The second elastic members 304 abut against the bottom of the head 324. The third retainer ring 310 fits around the inner ring portion of the second stopper ring 316, and both abut against the bottom of the second elastic members 304. The fourth retainer ring 312 abuts the bottom of the second stopper ring 316. This assembly is placed in one half 401 of the cylindrical case 206 so the head 324 protrudes into the mid-bore 406 and abuts the head 318, the second elastic members 304 abut the bottom of the second counterbore 404, the third retainer ring 310 fits in the inner circumferential cutout 412, and the fourth retainer ring 312 fits in the outer circumferential cutout 414. Note that another set of through holes 208 are defined in the cylindrical case 206 around the second stopper ring 316. The two halves 401 are then fixed by welding or other methods.

In an initial example configuration, the first stopper ring 314 is fixed by the first retainer ring 306 and the second retainer ring 308. In turn, the first stopper ring 314 prevents the first rod 202 from translating outward and rotating. Similarly, the second stopper ring 316 is fixed by the third retainer ring 310 and the fourth retainer ring 312. In turn, the second stopper ring 316 prevents the second rod 204 from translating outward and rotating. As the first rod 202 and the second rod 204 abut each other, they prevent each other from translating inward as well.

In an example operation, over time, bodily fluid enters through holes 208 and decomposes the first stopper ring 314 and the second stopper ring 316. With the first stopper ring 314 removed, the first rod is able to translate outward and rotate against the first elastic members 302. Similarly, with the second stopper ring 316 removed, the second rod 204 is able to translate outward and rotate against the second elastic members 304. Note that if rigid fixation is not desired, rod system 110 may be constructed without the stopper rings 314 and 316.

The two rods can translate outward independently of each other. One rod can also translate inward and push the other rod outward. The two rods can always rotate independently as they contact through their hemispheroid head 318 and 324. Together they allow the rod system 110 to provide six degrees-of-freedom.

Figure 6:
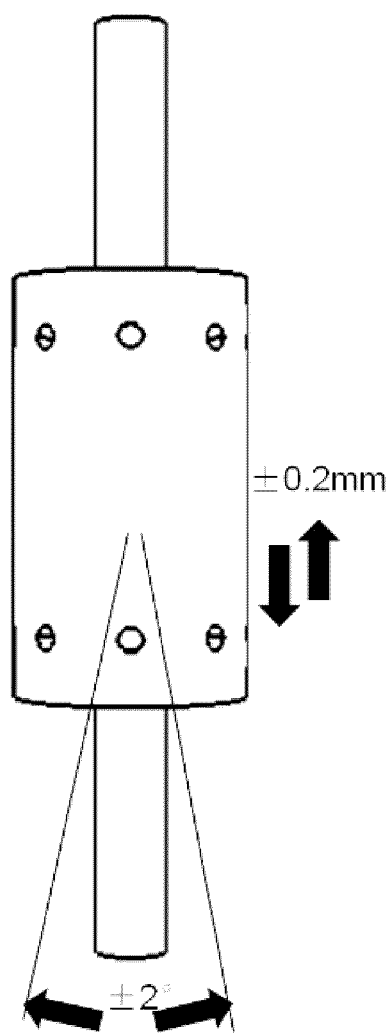
FIG. 6 is a front view of an illustrative translation and rotation of the rod system of FIG. 2, all arranged in accordance with at least some embodiments described herein.

In an embodiment, the resilience of elastic members 302 and 304 is selected to provide predetermined translation of the first rod 202 and the second rod 204. In one or more embodiments of the present disclosure, each rod may have an axial translation of about ±0.1 to 0.3 mm, such as ±0.2 mm, along each rod axis. The inner radii of retainer rings 308 and 312 are selected to larger than the radii of the shafts 322 and 328 provide a predetermined limit for frontal and the sagittal rotations of the first rod 202 and the second rod 204. In one or more embodiments of the present disclosure, each rod may have frontal and sagittal rotations of about ±1 to 3°, such as ±2°. FIG. 6 shows a front view of an illustrative translation and rotation of the rod system 110 of FIG. 2.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A rod system, comprising:
   a first rod having a first head and a first shaft;
   a first elastic member fitted around the first shaft and against the first head;
   a second rod having a second head and a second shaft;
   a second elastic member fitted around the second shaft and against the second head;
   an absorbable material that can be decomposed by bodily fluid; and
   a case defining:
      a first inner portion with a first outer opening;
      a second inner portion with a second outer opening; and
      a third inner portion in communication with the first and the second inner portions;
   wherein:
      the first rod with the first elastic member is seated in the first inner portion so the first elastic member abuts the bottom of the first inner portion and the first head protrudes into the third inner portion; and
      the second rod with the second elastic member is seated in the second portion so the second elastic member abuts the bottom of the second inner portion and the second head protrudes into the third inner portion and abuts the first head.

2. The system of claim 1, wherein the first elastic member comprise elastic washers.

3. The system of claim 1, wherein the second elastic member comprise elastic washers.

4. The system of claim 1, wherein the first and the second heads are substantially hemispheroid.

5. The system of claim 1, wherein the first and the second heads have treated surfaces to reduce friction between the first and the second heads.

6. The system of claim 1, further comprising a first retainer ring fixed to the first inner portion, the first retainer ring abuts the first elastic member so the first elastic member is sandwiched between the first retainer ring and the bottom of the first inner portion.

7. The system of claim 6, further comprising a second retainer ring fixed to the first inner portion, the second retainer ring having an inner radius larger than a radius of the shaft.

8. The system of claim 7, further comprising a first stopper ring between the first and the second retainer rings, wherein the first stopper ring is made of the absorbable material, wherein the first stopper ring prevents movement to the first rod.

9. The system of claim 8, wherein the first stopper ring comprises a first portion and a second portion, the first portion having an inner radius substantially equal to a radius of the first shank, the second portion having an inner radius substantially equal to a radius matching a second radius of a first neck of the first rod between the first head and the first shaft.

10. The system of claim 9, further comprising:
a third retainer ring fixed to the second inner portion, the third retainer ring abuts the second elastic member so the second elastic member is sandwiched between the third retainer ring and the bottom of the second inner portion; and
a fourth retainer ring fixed to the second inner portion, the fourth retainer ring having a radius larger than a radius of the second shaft.

11. The system of claim 10, further comprising a second stopper ring between the third and the fourth retainer rings, the second stopper ring preventing movement to the second rod, the second stopper ring comprising an absorbable material that can be decomposed by bodily fluid.

12. The system of claim 11, wherein the second stopper ring comprises a third portion and a fourth portion, the third portion having an inner radius substantially equal to a radius of the second shank, the fourth portion having an inner radius substantially equal to a second neck of the second rod between the second head and the second shaft.

13. The system of claim 9, wherein the case defines a plurality of through holes to the first stopper ring so that bodily fluid is able to contact and decompose the first stopper ring over time to allow movement to the first rod.

14. The system of claim 12, wherein the case defines a plurality of through holes to the first and the second stopper ring so that bodily fluid is able to contact and decompose the first and the second stopper rings over time to allow movement to the first and the second rods.

15. A bone fixation system, comprising:
a rod system, comprising:
a first elastic member;
a first rod having a first head and a first shaft, the first rod passing through the first elastic member until the first head abuts the first elastic member;
a second elastic member;
a second rod having a second head and a second shaft, the second rod passing through the second elastic member until the second head abuts the second elastic member;
an absorbable material that can be decomposed by bodily fluid; and
a case defining a first inner portion with a first outer opening, a second inner portion with a second outer opening, and a third inner portion in communication with the first and the second inner portions;
wherein:
the first elastic member with the first rod is seated in the first inner portion until the first elastic member abuts the bottom of the first inner portion and the first head protrudes into the third inner portion; and
the second elastic member with the second rod is seated in the second portion until the second elastic member abuts the bottom of the second inner portion and the second head protrudes into the third inner portion and abuts the first head;
a first bone screw connected to the first rod; and
a second bone screw connected to the second rod.

16. A case, comprising:
a first inner portion with a first outer opening, the first inner portion defining first and second circumferential cutouts;
a first plurality of through holes to the first inner portion;
a second inner portion with a second outer opening, the second inner portion defining third and fourth circumferential cutouts;
a second plurality of through holes to the second inner portion;
an absorbable material that can be decomposed by bodily fluid; and
a third inner portion in communication with the first and the second inner portions.

* * * * *